United States Patent [19]

Osieka et al.

[11] 3,969,510

[45] July 13, 1976

[54] METHOD OF CONTROLLING FUNGI

[75] Inventors: Hans Osieka, Ludwigshafen; Ernst-Heinrich Pommer, Limburgerhof; Hans Kiefer, Wachenheim, all of Germany

[73] Assignee: Badische Anilin- & Soda-Fabrik Aktiengesellschaft, Ludwigshafen (Rhine), Germany

[22] Filed: June 9, 1975

[21] Appl. No.: 584,859

Related U.S. Application Data

[63] Continuation of Ser. No. 234,982, March 15, 1972, abandoned, which is a continuation of Ser. No. 53,307, July 8, 1970, abandoned, which is a continuation-in-part of Ser. No. 722,549, April 19, 1968, abandoned.

[30] Foreign Application Priority Data

Apr. 28, 1967 Germany.............................. 1642224

[52] U.S. Cl. ................................................ 424/324
[51] Int. Cl.² .......................................... A01N 9/20
[58] Field of Search ..................................... 424/324

[56] References Cited
UNITED STATES PATENTS

| | | | |
|---|---|---|---|
| 2,643,965 | 6/1953 | O'Brien et al. ..................... | 424/324 |
| 3,311,562 | 3/1967 | Stecker ............................... | 424/324 |
| 3,428,669 | 2/1969 | Gier et al. .......................... | 424/300 |

OTHER PUBLICATIONS

*Chemical Abstracts,* vol. 47 (1953), 8041; vol. 65 (1966), 15282–15283.

*Primary Examiner*—Frederick E. Waddell
*Attorney, Agent, or Firm*—Johnston, Keil, Thompson & Shurtleff

[57] ABSTRACT

Method of controlling fungi with substituted benzoic acid derivatives, in particular substituted benzanilides.

9 Claims, No Drawings

METHOD OF CONTROLLING FUNGI

RELATED APPLICATIONS

This application is a continuation of our abandoned application Ser. No. 234,982, filed Mar. 15, 1972, which in turn is a continuation of our abandoned application Ser. No. 53,307, filed July 8, 1970 which in turn is a continuation-in-part of our abandoned application Ser. No. 722,549, filed Apr. 19, 1968.

The present invention relates to a method of controlling fungi or for protecting objects from fungous diseases, in particular for protecting plants from fungous attack by treatment with substituted benzoic acid derivatives, especially substituted benzanilides.

It is known that tetramethylthiuram disulfide may be used for controlling fungi. However its action is not satisfactory.

An object of the present invention is to provide a method of controlling fungi. Another object of the invention is to provide a method of preventing plants from being affected by fungi. A further object of the invention is to provide a method of controlling fungi with substituted benzoic acid derivatives.

These and other objects of the invention are achieved with compounds having the formula

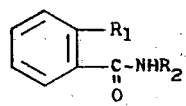

in which $R^1$ denotes lower alkyl, chloro, bromo, iodo, trifluoromethyl, nitro or amino and $R_2$ denotes phenyl or cycloalkyl of 6-8 carbon atoms. They exhibit good action on injurious fungi, especially from the class of Basidiomycetes, e.g., Rhizoctonia, Coniophora, Tilletia, Puccinia and Ustilago.

The active ingredients may be prepared by known methods, e.g., by reacting a carboxylic acid having the formula

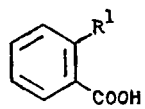

in which $R^1$ has the meanings given above, or an ester, anhydride, or halide of this acid with an amine having the formula $H_2N-R_2$. $R_2$ having the meaning given above.

By organic or inorganic acids we mean for example the following acids: hydrochloric acid, hydriodic acid, hydrobromic acid, sulfuric acid, acetic acid, propionic acid, benzoic acid, oxalic acid, malonic acid, phthalic acid, isophthalic acid, terephthalic acid and benzenesulfonic acid.

The preparation of the active ingredients is illustrated by the following examples (in which parts are by weight).

Preparation of 2-methylbenzoic cyclohexylamide 9.9 parts of cyclohexylamine is dissolved in 100 parts of benzene and the mixture is reacted with 15.5 parts of 2-methylbenzoyl chloride in the presence of 12 parts of triethylamine at 10°C. The whole is stirred for 3 hours at 60°C and then cooled; the precipitated triethylamine chloride is filtered, the filtrate is concentrated under vacuum and the residue is recrystallized from a mixture of methanol and water.

Yield: 90% of the theory; melting point: 132°C.

The following compounds are examples of the active ingredients:

|  | m.p. |
|---|---|
| 2-methylbenzoic cyclohexylamide | 132°C |
| 2-methylbenzoic cyclooctylamide | 113 to 115°C |
| 2-bromobenzanilide | 117 to 119°C |
| 2-trifluoromethylbenzanilide | 151 to 152°C |
| 2-methylbenzanilide | 126°C |
| 2-nitrobenzanilide | 155°C |
| 2-aminobenzanilide | 130 to 131°C |
| 2-chlorobenzanilide | 115°C |
| 2-iodobenzanilide | 143 to 144°C |

The agents according to this invention may be used as solutions, emulsions, suspensions or dusts. The form of application depends entirely on the purpose for which the agents are being used; in any case it should ensure a fine distribution of the active ingredient.

For the preparation of solutions to be sprayed direct, mineral oil fractions with medium to high boiling points such as kerosene or diesel oil, coal-tar oils and oils of vegetable and animal origin, cyclic hydrocarbons, such as tetrahydronaphthalene, and alkylated naphthalenes are suitable.

Aqueous formulations may be prepared from emulsion concentrates, pastes or wettable powders by adding water. To prepare emulsions the ingredients as such or dissolved in a solvent may be homogenized in water by means or wetting or dispersing agents. Concentrates which are suitable for dilution with water may be prepared from active ingredient, emulsifying or dispersing agent and possibly solvent.

Dusts may be prepared by mixing or grinding the active ingredients with a solid carrier. The salts of the active ingredients may also be used in the form of their aqueous solutions.

The good fungicidal properties of the agents are illustrated by the following Examples.

EXAMPLE 1

The active ingredients are dissolved in acetone and dispersed in a nutrient agar (malt) as described in Example 1. The agar is then similarly inoculated with small flakes of mycelium of *Coniophora cerebella*. The fungus is incubated for 6 days at 25°C and the extent of the development of the fungus colonies is then assessed. The results are shown in the Table below in which

| Active ingredient | Coniophora cerebella % active ingredient in agar | | |
|---|---|---|---|
| | 0.05 | 0.025 | 0.01 |
| 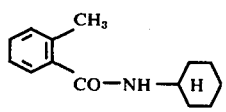 | 1 | 1 | 2 |
| Tetramethylthiuram disulfide (TMTD) | 1 | 3 | 4 |
| Control | | | 5 |

| Active ingredient | Coniophora cerebella % active ingredient in agar | | |
|---|---|---|---|
| | 0.05 | 0.025 | 0.01 |
| (untreated) | | | |

0 = no fungous growth
1 = diameter of fungus colony 0.5 to 1 cm
2 = diameter of fungus colony 1 to 2 cm
3 = diameter of fungus colony 2 to 2.5 cm
4 = diameter of fungus colony 2.5 to 4 cm
5 = diameter of fungus colony 4 to 5 cm

EXAMPLE 2

The active ingredients are thoroughly triturated in amounts of 20 and 40% (by weight) with talc. 0.01 g of spores of wheat bunt (*Tilletia tritici*) is thoroughly dispersed with 0.2 g of the mixture of active ingredient and talc and the whole is dusted onto 10 g of puddled earth in Petri dishes having a diameter of 5 cm. The dishes are then kept in a refrigerator for ten days at 10° to 12°C. By this time the spores in the control dish (mixture of spores and talc) have germinated and the action of the agents in the other dishes can be assessed as follows:

| Active ingredient | Tilletia tritici % active ingredient in mixture | |
|---|---|---|
| | 20 | 40 |
| [2-methylbenzanilide structure: benzene ring with CH₃ and CO—NH-phenyl] | + | 0 |
| Control (Mixture of spores + talc) | +++ | +++ |

+++ = vigorous germination, as in control
++ = clearly reduced germination
+ = considerably reduced germination, only sporadic
0 = complete inhibition of germination

EXAMPLE 3

The active ingredients are dissolved in acetone in amounts of 0.05, 0.025 and 0.01% (by weight) and thoroughly dispersed in a still liquid nutrient agar (malt). The agar is poured out into Petri dishes with a diameter of 5 cm. After the agar has solidified the dishes are inoculated in the centre with small flakes of mycelia of *Rhizoctania solani* and *Coniophora cerebella*. The fungi are incubated at 25°C and after 6 (*Rhizoctonia*) or 4 (*Coniophora*) days the extent of the development of the fungus colonies is assessed. The results are shown in the Table below in which

| Active ingredient | Rhizoctonia solani % active ingredient in agar | | | Coniophora cerebella % active ingredient in agar | | |
|---|---|---|---|---|---|---|
| | 0.05 | 0.25 | 0.01 | 0.05 | 0.025 | 0.01 |
| [benzanilide with 2-CH₃] | 0 | 0 | 1 | 0 | 0 | 0 |
| [benzanilide with 2-Cl] | 0 | 0 | 0 | 0 | 0 | 0 |
| [benzanilide with 2-NO₂] | 0 | 0 | 0 | 0 | 0 | 0 |
| [benzanilide with 2-CF₃] | 0 | 0 | 0 | 0 | 0 | 0 |
| [benzanilide with 2-NH₂] | 0 | 0 | 1 | 0 | 0 | 2 |
| [benzanilide with 2-Br] | 0 | 0 | 0 | 0 | 0 | 0 |
| Tetramethylthiuram disulfide (TNTD) (comparative agent) | 2 | 3 | 5 | 1 | 3 | 4 |
| Control (untreated) | | | 5 | | | 5 |

0 = no fungous growth
1 = diameter of fungus colony 0.5 to 1 cm
2 = diameter of fungus colony 1 to 2 cm
3 = diameter of fungus colony 2 to 2.5 cm
4 = diameter of fungus colony 2.5 to 4 cm
5 = diameter of fungus colony 4 to 5 cm

EXAMPLE 4

Leaves of pot grown oat seedlings are artificially infected with spores of crown rust (*Puccinia coronata*) and placed in a chamber saturated with water vapor for 24 hours at 18° to 20°C. The plants are then sprayed with aqueous emulsions of a mixture of 80% active ingredient and 20% emulsifying agent and then left for 10 days in a greenhouse at temperatures between 20° and 22°C and where the relative air humidity is 75 to 80%. The extent of the development of the rust fungus is then assessed.

| Active ingredient | Extent of attack after spraying with % liquor | |
|---|---|---|
| | 0.1 | 0.05 |
| (2-methyl benzanilide structure) | 1 | 2 |
| (2-iodo benzanilide structure) | 0 | 0 |
| Control (untreated) | 8 | |

0 = no attack
graduated up to 10 = total attack

We claim:

1. A method of controlling fungi of the class *Basidiomycetes* which comprises contacting fungi of the class *Basidiamycetes* with a fungicidally effective amount of a compound having the formula

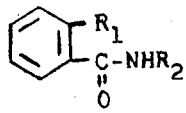

in which $R_1$ denotes methyl, chloro, bromo, iodo, trifluormethyl, amino or nitro and $R_2$ denotes phenyl or cycloalkyl of 6-8 carbon atoms.

2. The method of claim 1 wherein said fungi are one or more of *Rhizoctonia*, *Coniophora*, *Tilletia*, *Puccinia* and *Ustilago*.

3. The method of claim 1 wherein said compound is 2-methylbenzanilide.

4. The method of claim 1 wherein said compound is 2-chlorobenzanilide.

5. The method of claim 1 wherein said compound is 2-iodobenzanilide.

6. The method of claim 1 wherein said compound is 2-bromobenzanilide.

7. The method of claim 1 wherein said compound is 2-nitrobenzanilide.

8. The method of claim 1 wherein said compound is 2-methylbenzoic cyclohexylamide.

9. The method of claim 1 wherein said fungicidally effective amount of said compound is sprayed on plants infested with said fungi.

* * * * *